United States Patent
Shang et al.

(10) Patent No.: US 11,707,246 B2
(45) Date of Patent: Jul. 25, 2023

(54) METHOD AND APPARATUS FOR AUTOMATIC DETERMINATION OF OBJECT AND BACKGROUND REGION OF INTEREST FOR REAL-TIME AUTOMATIC DOSE RATE CONTROL IN DYNAMIC IMAGING SYSTEMS

(71) Applicant: CANON MEDICAL SYSTEMS CORPORATION, Tochigi (JP)

(72) Inventors: Weifeng Shang, Vernon Hills, IL (US); Joseph Manak, Vernon Hills, IL (US); John Baumgart, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 288 days.

(21) Appl. No.: 17/070,546

(22) Filed: Oct. 14, 2020

(65) Prior Publication Data

US 2022/0110602 A1 Apr. 14, 2022

(51) Int. Cl.
*A61B 6/00* (2006.01)
*G06T 7/11* (2017.01)

(52) U.S. Cl.
CPC .............. *A61B 6/542* (2013.01); *A61B 6/487* (2013.01); *A61B 6/5258* (2013.01); *G06T 7/11* (2017.01);
(Continued)

(58) Field of Classification Search
CPC . G06T 7/11; G06T 7/194; G06T 2207/30021; G06T 2207/20081; G06T 2207/30004; G06T 2207/10121; G06T 2207/20084; G06T 7/74; G06T 7/001422; G06T 2207/10081; G06T 11/00; G06T 11/008; G06T 7/0014; G06T 11/006; G06T 5/002; G06T 5/50; G06T 2211/424; G06T 2207/30196; G06T 7/0012; G06T 2207/10056; G06T 2207/10064; G06T 2207/20021; G06T 2207/30024; G06T 5/003; G06T 3/40; G06T 5/20; G06T 7/143; G06T 2207/10116; G06T 2207/20116;
(Continued)

(56) References Cited

U.S. PATENT DOCUMENTS 5,838,758 A * 11/1998 Krug .................... G01V 5/0041
378/53
8,401,270 B2 * 3/2013 Eilbert ................. G01V 5/0033
250/306

(Continued)

*Primary Examiner* — Irakli Kiknadze
(74) *Attorney, Agent, or Firm* — Oblon, McClelland, Maier & Neustadt, L.L.P.

(57) ABSTRACT

A method of imaging includes obtaining a first image including projection data representing an intensity of X-rays detected by a plurality of detectors at a first X-ray exposure setting, the X-rays being emitted from an X-ray source; based on a detection result of a first object in the first image: determining a background region of interest (ROI) around the first object, the background ROI including background ROI pixels having a first intensity value corresponding to the intensity of the X-rays; and converting, for each pixel of the background ROI pixels, the first intensity values of the background ROI pixels to a normalized X-ray attenuation factor; and determining a second X-ray exposure setting for use in obtaining a second image based on the background ROI pixels converted to the normalized X-ray attenuation factor.

23 Claims, 7 Drawing Sheets

(52) U.S. Cl.
CPC ............... *G06T 2207/10121* (2013.01); *G06T 2207/20081* (2013.01); *G06T 2207/20084* (2013.01); *G06T 2207/30004* (2013.01)

(58) Field of Classification Search
CPC . G06T 2207/30036; G06T 2207/20032; G06T 7/12; G06T 2207/30096; G06T 11/206; G06T 7/0004; G06T 5/008; G06T 7/155; G06T 7/20; G06T 7/0016; G06T 7/70; A61B 6/542; A61B 6/12; A61B 6/5258; A61B 6/487; A61B 6/501; A61B 6/032; A61B 6/04; A61B 6/469; A61B 6/06; A61B 6/4405; A61B 6/566; A61B 6/5223; A61B 6/567; A61B 6/461; A61B 6/5294; A61B 6/467; A61B 6/466; A61B 6/5247; A61B 6/563; A61B 6/4452; A61B 6/0407; A61B 6/546; A61B 6/4441; A61B 6/4417; A61B 6/547; A61B 6/465; A61B 6/0467; A61B 6/102; A61B 6/504; A61B 6/5205; A61B 6/4447; A61B 6/5282; A61B 6/4014; A61B 6/463; A61B 6/4241; A61B 6/502; A61B 6/482; A61B 6/5217; A61B 6/483; A61B 6/14; A61B 6/505; A61B 6/00; A61N 5/1069; A61N 5/1049; A61N 5/1039; A61N 5/1038; A61N 5/1031; A61N 5/10; A61N 2005/1062; A61N 2005/1061; A61N 5/1067; G06V 10/24; G06V 10/25; G06V 2201/031; G06V 20/693; G06V 10/462; G06V 20/695; G06V 10/764; G06V 20/647; G06V 10/82; G06V 10/763; G16H 30/40; G16H 50/20; G16H 30/20; G16H 50/70; G16H 50/30; G01N 33/53; G01N 23/044; G01N 23/087; G01N 23/083; G01N 23/18; G01N 2223/423; G01N 2223/402; G01N 2223/652; G01N 33/02; G01N 23/04; G06N 20/00; G06N 3/08; G06N 3/0454; G01V 5/0016; G01V 5/0041; G01V 5/005; G06F 18/23213
USPC ........................................... 378/4, 16, 19, 62
See application file for complete search history.

(56) References Cited

U.S. PATENT DOCUMENTS

| | | | |
|---|---|---|---|
| 10,115,197 B1* | 10/2018 | Alsmadi | .................. A61B 6/14 |
| 2012/0014586 A1 | 1/2012 | Kosarev | |
| 2015/0366525 A1 | 12/2015 | Sandholm et al. | |
| 2016/0082289 A1 | 3/2016 | Frigo | |
| 2018/0338742 A1 | 11/2018 | Singh et al. | |
| 2019/0162679 A1* | 5/2019 | Yamakawa | .......... G01N 23/044 |
| 2020/0360729 A1* | 11/2020 | Sun | ........................ G06V 10/24 |
| 2021/0118131 A1* | 4/2021 | Chae | .................... A61B 6/5205 |

* cited by examiner

METHOD AND APPARATUS FOR AUTOMATIC DETERMINATION OF OBJECT AND BACKGROUND REGION OF INTEREST FOR REAL-TIME AUTOMATIC DOSE RATE CONTROL IN DYNAMIC IMAGING SYSTEMS

FIELD OF THE INVENTION

This disclosure relates to identify and localizing an object and background region of interest, or a main region of interest, in an image generated by a fluoroscopy system. The dose rate for the next pulse of radiation is automatically adjusted to improve contrast to noise ratio in the subsequent image.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

X-ray imaging systems and methods are widely used medical imaging tools for diagnosis and clinical interventions. Radiography systems are essential tools in interventional radiology procedures which may vary from a few minutes to several hours. Radiography systems generally create two-dimensional projection images through a subject's body. A radiation source, such as an X-ray tube, irradiates the body from one side. A collimator, generally adjacent to the X-ray source, limits the angular extent of the X-ray beam, so that radiation impinging on the body is substantially confined to a cone-beam/fan-beam region (i.e., an X-ray projection volume) defining an image volume of the body. At least one detector on the opposite side of the body receives radiation transmitted through the body substantially in the projection volume. The attenuation of the radiation that has passed through the body is measured by processing electrical signals received from the detector.

In both fluoroscopic mode and acquisition mode, a sequence of X-ray exposures is collected at a selected frame rate. During the procedure, the patient anatomy and the imaging geometry, such as Source-to-Imager Distance (SID) and angulation, may change frequently according to the radiologists' need.

Some systems are equipped with automatic dose rate control (ADRC) to dynamically adjust the X-ray technique parameters in order to maintain image quality as such changes occur. Some implemented ADRC systems aim to maintain the image brightness or the detector pixel value of a specific region of interest (ROI) to a target level as long as the technical limits of the system and the regulation dose limits allow. It is also the responsibility of ADRC to ensure that the patient skin dose is optimized, minimizing the dose to the patient required to see objects of interest, while maximizing image quality. One of the consequences of this approach is that the contrast to noise ratio (CNR), which is a measurement of object visibility, of some object of interest (e.g. guide wires or iodinated blood vessel) decreases significantly as the patient thickness increases or higher density materials are introduced into the field of view of the image. As a result, such objects may become invisible in thicker patients. Thus, a method and apparatus is desired to extract the target object and background information essential to ADRC automatically for real-time, closed-loop ADRC to optimize X-ray parameters to achieve a target CNR.

SUMMARY

The present disclosure relates to an imaging apparatus, including: processing circuitry configured to obtain a first image including projection data representing an intensity of X-rays, emitted from an X-ray source, detected by a plurality of detectors at a first X-ray exposure setting, based on a detection result of a first object in the first image: determine a background region of interest (ROI) around the first object, the background ROI including background ROI pixels having a first intensity value corresponding to the intensity of the X-rays, and convert, for each pixel of the background ROI pixels, the first intensity values of the background ROI pixels to a normalized X-ray attenuation factor, and determine a second X-ray exposure setting for use in obtaining a second image based on the background ROI pixels converted to the normalized X-ray attenuation factor.

The disclosure additionally relates to a method of imaging, including: obtaining a first image including projection data representing an intensity of X-rays detected by a plurality of detectors at a first X-ray exposure setting, the X-rays being emitted from an X-ray source; based on a detection result of a first object in the first image: determining a background region of interest (ROI) around the first object, the background ROI including background ROI pixels having a first intensity value corresponding to the intensity of the X-rays; and converting, for each pixel of the background ROI pixels, the first intensity values of the background ROI pixels to a normalized X-ray attenuation factor; and determining a second X-ray exposure setting for use in obtaining a second image based on the background ROI pixels converted to the normalized X-ray attenuation factor.

Note that this summary section does not specify every embodiment and/or incrementally novel aspect of the present disclosure or claimed invention. Instead, this summary only provides a preliminary discussion of different embodiments and corresponding points of novelty. For additional details and/or possible perspectives of the invention and embodiments, the reader is directed to the Detailed Description section and corresponding figures of the present disclosure as further discussed below.

BRIEF DESCRIPTION OF THE DRAWINGS

Various embodiments of this disclosure that are proposed as examples will be described in detail with reference to the following figures, wherein like numerals reference like elements, and wherein.

DETAILED DESCRIPTION

Figure 1:
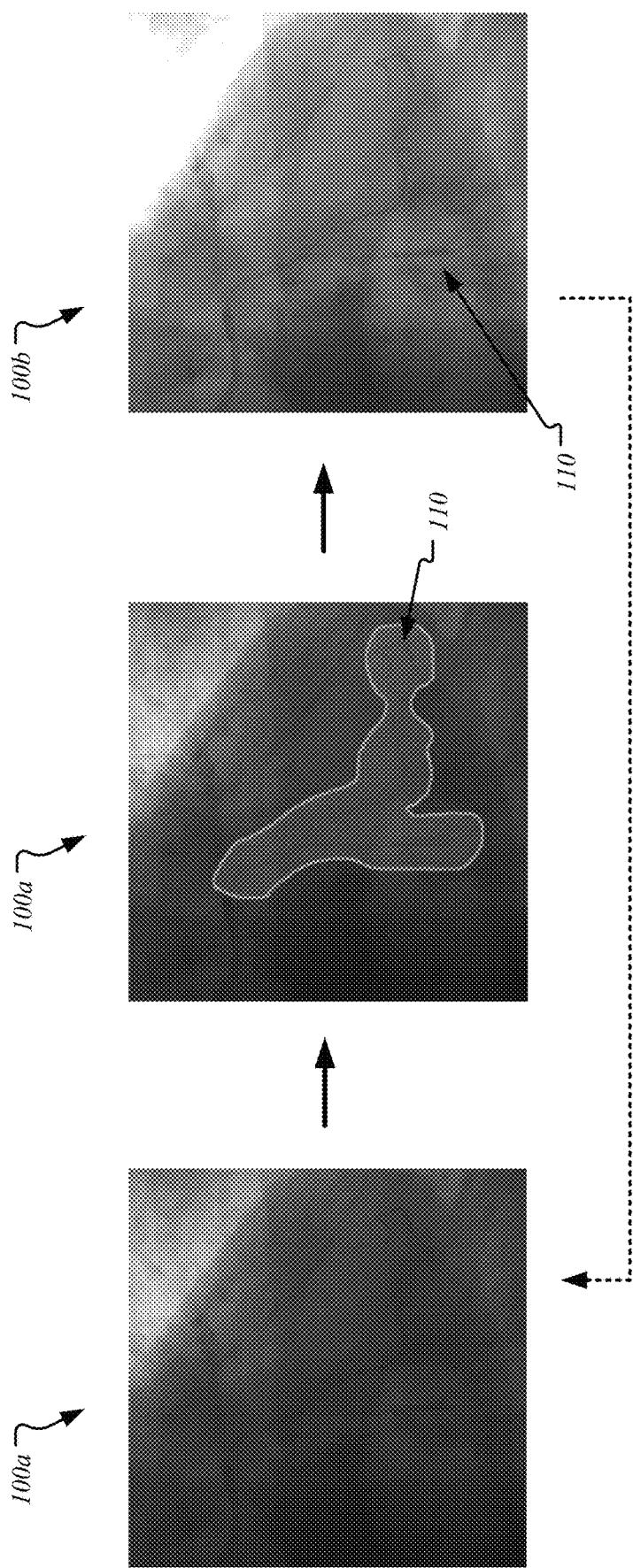
FIG. 1 shows example images for a non-limiting example process flow overview for automatically adjusting an automatic dose rate control (ADRC), according to an embodiment of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed. Further, spatially relative terms, such as "top," "bottom," "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The order of discussion of the different steps as described herein has been presented for clarity sake. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways.

In clinical practice, an object of interest for a radiologist or operator varies frequently (for example from a guide wire, to a catheter, iodinated blood vessel, or a stent) during the interventional procedure. If such information is manually input, it can be a tedious task for the operator and can introduce errors. Importantly, incorrect object information can lead to non-optimal X-ray techniques for X-ray exposure, which can cause unnecessary dose penalty or negatively impact the visibility of the object.

Patient thickness, another important input of automatic dose rate control (ADRC), is usually estimated from averaged pixel values within a defined region of interest (ROI). If some bone structures, such as a spine, or unexpected materials, such as from pacemakers, are located in the ROI, the thickness estimation is usually under-estimated because the soft tissue region in the ROI is averaged. In such cases, the contrast to noise ratio (CNR) of the interested object cannot be kept at a pre-defined level and may lead to worse object visibility than that which the system could deliver.

The exposure parameters can be optimized and realized when accurate information about the object and a normalized X-ray attenuation factor (e.g., a thickness with equivalent attenuation of predetermined materials such as water, acrylic, aluminum, and bone etc., or a combination of various thickness values of various materials) of the patient at the vicinity of the clinically relevant object can be obtained in real-time. In a dynamic imaging system, the X-ray images can be generated in a sequence of frames at a certain rate during operation. As such, ADRC can use information from a current frame to adjust exposure parameters for a subsequent frame.

As described herein, a method includes obtaining necessary object and background information to automatically adjust an ADRC and achieve a target CNR. Computer vision can be used to identify various types of objects or regions present in images, including i) objects of interest, such as guide wires, contrasted vasculature, stent markers, and catheter tips, ii) objects to exclude, such as pacemakers, dental work, aneurysm coils, and hip replacements, and iii) a background region around the object. Various techniques can be used to implement the computer vision identification, including a deep neural network (DNN), machine learning techniques, computer vision techniques, or any combination thereof.

FIG. 1 shows example images for a non-limiting example process flow overview for automatically adjusting the ADRC, according to an embodiment of the present disclosure. In an embodiment, a first image 100a is obtained via a fluoroscopy system with a first X-ray exposure setting. The fluoroscopy system can include an X-ray source configured to emit X-ray radiation at a predetermined intensity and processing circuitry, such as a computer, to analyze any images obtained by the fluoroscopy system. Notably, the first image 100a can be under exposed, as shown, and not of sufficient quality for a user, such as a technician or medical profession, to interpret. It may be appreciated that the first image 100a can be over exposed in some cases. However, the first image 100a can still be analyzed by the processing circuitry to identify any objects present in the first image 100a, for example a guide wire 110. In the under exposed first image 100a, the processing circuitry can determine a location of the guide wire 110 and segment a region of interest 115 around the guide wire 110 as a background. Information about the guide wire 110 and the background around the guide wire 110 can be used as inputs for an ADRC system or process to generate, via the processing circuitry, a second X-ray exposure setting with optimized exposure parameters for obtaining a second image 100b. The second image 100b can be of sufficient quality for the user to interpret after being obtained with the optimized exposure parameters, or in the case of still being of insufficient quality, the second image 100b can be analyzed by the processing circuitry to further refine the exposure parameters. The guide wire 110 in the second image 100b, as shown, can be better contrasted against the background as compared to the first image 100a.

Figure 2A:
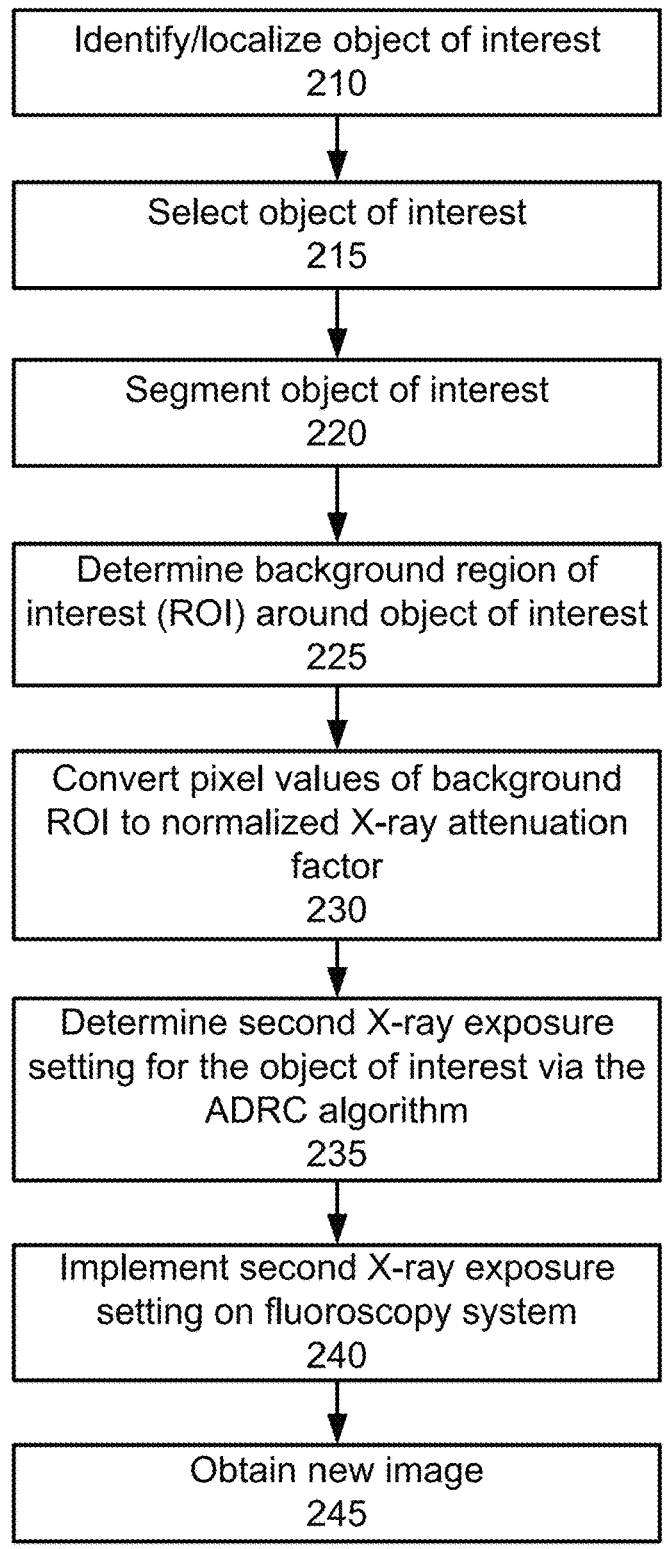
FIG. 2A shows a non-limiting example of a flow chart for a method of generating and applying optimized exposure parameters in a fluoroscopy system, according to an embodiment of the present disclosure.

A more detailed description of the automatic ADRC adjustment process flow is described herein with reference to FIG. 2A. FIG. 2A shows a non-limiting example of a flow chart for a method 200 of generating and applying optimized exposure parameters in the fluoroscopy system, according to an embodiment of the present disclosure. The objects of potential interest, like guide wires, stent markers, or vessels filled with contrast, can be identified and localized in an image in step 210. The processing circuitry can process an x-ray frame (i.e. the first image) and determine locations of various potential objects of interest. Objects to be excluded from measurement can also be identified. The location of the objects can be determined via machine vision, such as a deep neural network, traditional machine learning techniques, traditional computer vision techniques, or combinations thereof. In general, a neural network operates on an input by using a series of convolutional layers and other input data transformations, to produce an output which the network was trained to produce given similar inputs. With respect to ADRC adjustment, the neural network is trained to classify objects and determine their locations within an image. Such a neural network may produce a "heat map" showing the likelihood of each image pixel being a specific object, permitting extraction of region-of-interest information from the heat map. An alternative neural network may produce bounding boxes containing detectable objects within the input image from which the location of the desired object will be known. Alternatively, the user can manually determine and input the location of the objects.

The objects can be selected in step 215. A manual input from a user can be used to select the objects or an automated process can be used to determine which of the localized objects is of interest. The objects can be segmented from the first image in step 220.

From this information, a background ROI only in the vicinity of said objects can be determined automatically from the first image in step 225. Optionally, the background region can be selected to be of a relatively homogeneous pixel intensity, excluding adjacent regions close to the objects that may be considerably brighter (e.g., air) or darker (e.g., diaphragm adjacent to coronary arteries, contrast-filled bladder, pacemaker battery). It can be appreciated that pixel intensity can mean any measurable metric of the pixels in the first image, such as brightness. Thus, nearby neighbor pixels can be selected based on, for example, brightness within a predetermined threshold from a reference pixel's brightness. Objects to exclude that are identified may also be masked out of the background regions.

Once the background ROI for the objects is determined, the pixel values for the background ROI can be converted to a normalized X-ray attenuation factor (e.g., an equivalent thickness of water attenuation or bone attenuation, or a combination of various thicknesses of various materials) in step 230. The normalized X-ray attenuation factor can be estimated as the following: the averaged detector signal of the determined background ROI provides the information about the X-ray intensity transmitted through the patient's body while the exposure parameters of the X-ray source yields the information of the incident X-ray intensity. Given the incident and transmitted X-ray intensity, the X-ray attenuation of the patient's body can be determined. The attenuation values can then be converted to the normalized X-ray attenuation factor values via a lookup table including, for example, experimental results. The normalized X-ray attenuation factor can describe how much of the primary X-rays are attenuated before reaching the detector, wherein the primary X-rays are X-rays originating from the X-ray source instead of other sources, such as via scattering. In practice, the normalized x-ray attenuation factor for a given X-ray beam quality can be determined by the object thickness and the material composition of the object, which can be unknown when imaging patients. In some embodiments, it can be sufficient to characterize the imaged area as an equivalent thickness value of one type of material such as water, acrylic, or aluminum. In some embodiments, it is desirable to decompose the imaged area into multiple materials of various thicknesses. In both cases, the conversion of experimental attenuation value to the normalized attenuation factor can be done with pre-calculated lookup tables.

In a non-limiting example, the normalized X-ray attenuation factor can be determined per pixel location in the background ROI based on a map of material decomposition performed for each pixel location in the map. Upon determining material decomposition values (MDVs) for each pixel location in the material decomposition map corresponding to pixel locations in the selected background ROI, the background ROI pixels can be converted to the normalized X-ray attenuation factors in order to determine a new set of exposure parameters.

In a non-limiting example, the imaged area of the patient (with the objection of interest and the background ROI) can include more than one material, such as muscle and bone, along a first primary X-ray corresponding to a background ROI pixel value and location. For the same first primary X-ray, a two-parameter MDV can be determined for the corresponding background ROI pixel location (or a three-parameter MDV for three materials, a four-parameter MDV for four materials, etc.). The background ROI pixel value can be normalized based on the corresponding two-parameter material decomposition value to generate the normalized X-ray attenuation factor for the background ROI pixel at the same location (i.e. along the first primary X-ray). This can be performed for all background ROI pixels for all primary X-rays.

The ADRC process can determine the new set of exposure parameters for the X-ray system, which can include one or more of the tube voltage, tube current, focal spot size, pulse width, or other parameter that can be changed in real time between X-ray pulses. Notably, a library of objects information can be used by the ADRC process, wherein the objects information includes object material, type of object, and target CNR for optimal visibility. Thus, the objects information, background ROI information, current X-ray source parameters (e.g., kV, mA, pulse width) and real-time conditions (e.g., the anode temperature of the X-ray tube), and the target CNR can be used to determine, via the ADRC process and the processing circuitry, the second X-ray exposure setting with optimized exposure parameters in step 235.

These new parameters can be implemented by the fluoroscopy system for use for the next X-ray pulse in step 240. The ADRC process can also calculate the second X-ray exposure setting that can only be set while the fluoroscopy system is not active, such as a beam filter selection. These parameters (non-real time parameters) can be set in the fluoroscopy system at an appropriate time. Subsequently, the second image 100b can be obtained in step 245.

Figure 2B:
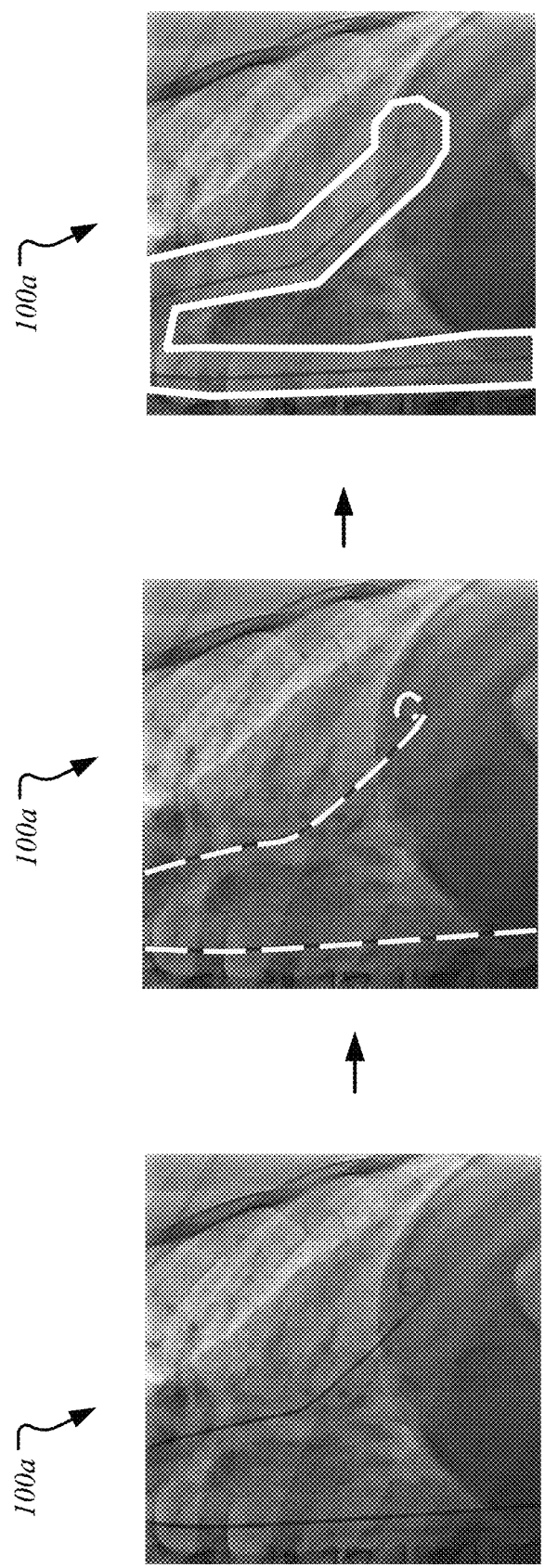
FIG. 2B shows example images for localizing an object of interest and determining a background region of interest, according to an embodiment of the present disclosure

FIG. 2B shows example images for localizing the object of interest and determining the background region of interest, according to an embodiment of the present disclosure. In an embodiment, the object can be localized from a first image (left image), such as via the dashed white line as shown (middle image). Once the object has been localized, a region of interest can be segmented around the guide wire as a background (right image).

Figure 3A:
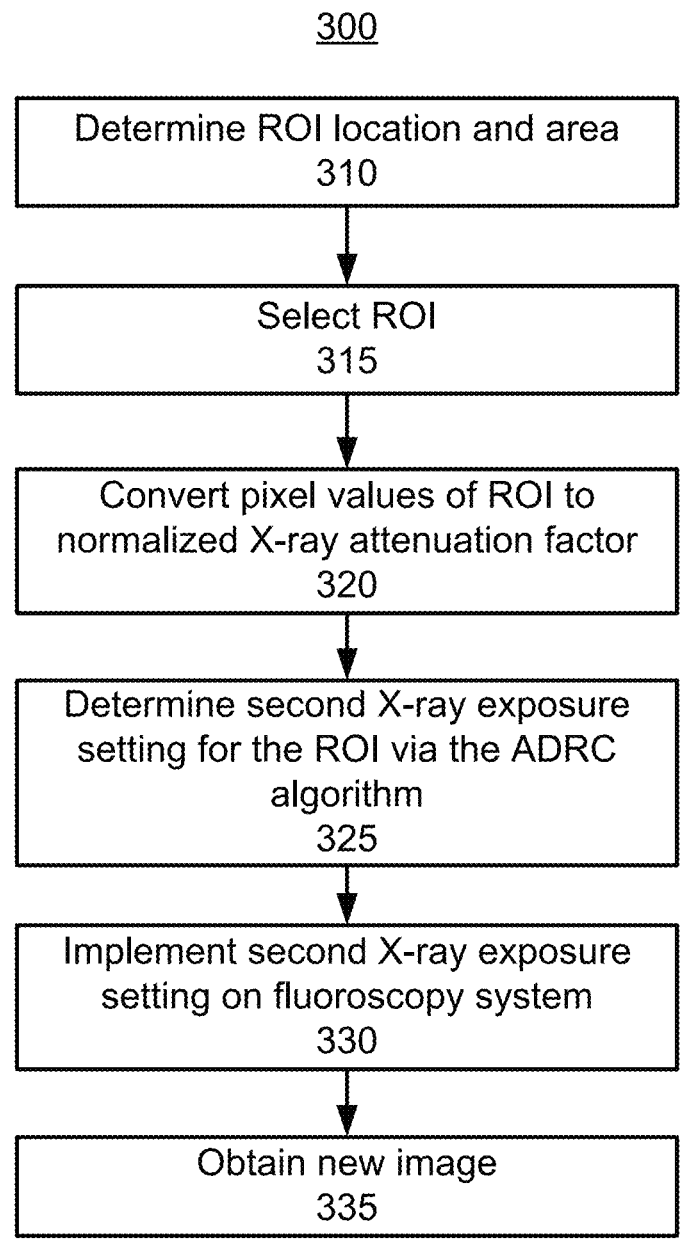
FIG. 3A shows a non-limiting example of a flow chart for a method of generating and applying optimized exposure parameters in a fluoroscopy system when no object is identified in a first image, according to an embodiment of the present disclosure.
Figure 3B:
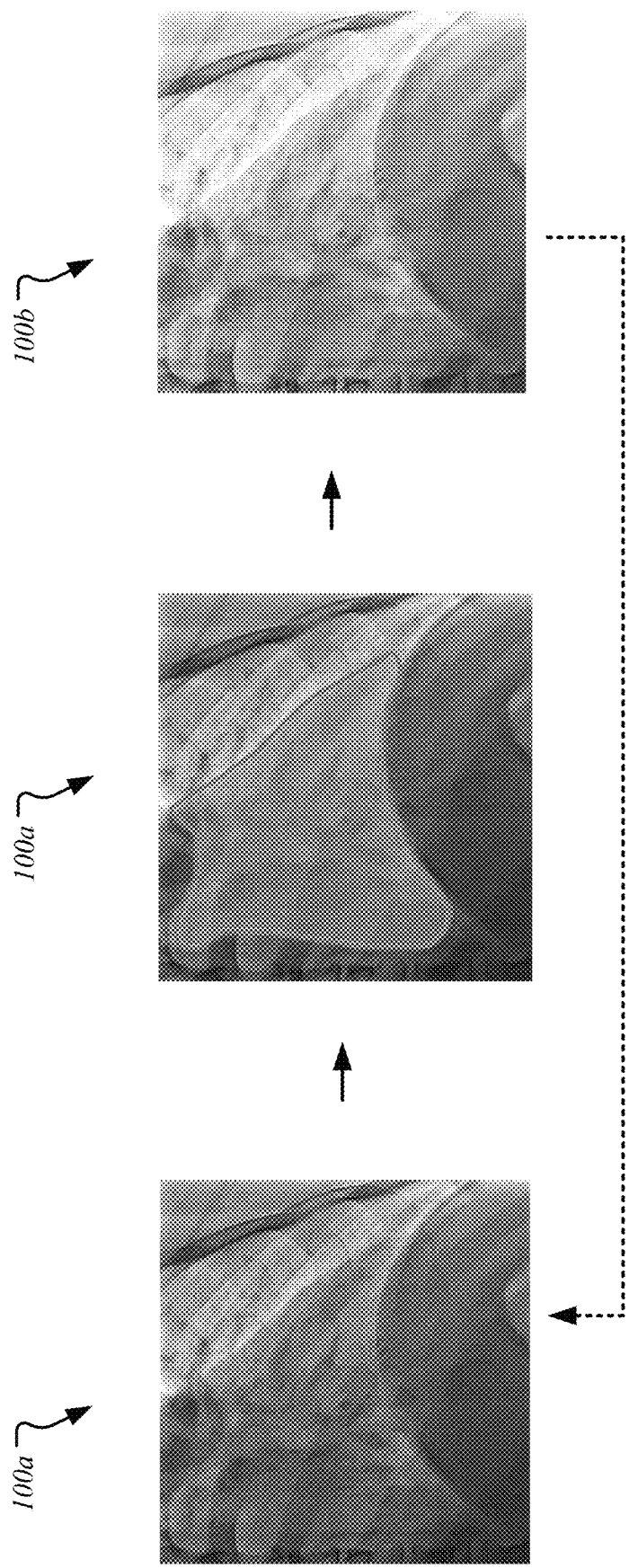
FIG. 3B shows example images for a non-limiting example process flow overview for automatically adjusting ADRC in the absence of an object, according to an embodiment of the present disclosure.

A more detailed description of the automatic ADRC adjustment process flow in FIG. 3B is described herein with reference to FIG. 3A. FIG. 3A shows a non-limiting example of a flow chart for a method 300 of generating and applying optimized exposure parameters in the fluoroscopy system when no object is identified in the first image, according to an embodiment of the present disclosure.

In the absence of an object in the first image 100a, the processing circuitry can determine that a main region of the first image is of interest (herein referred to as "main ROIs"). The processing circuitry can process the X-ray frame (i.e. the first image 100a) and determine locations of the various potential main ROIs. The main ROIs of the first image 100a can be determined, for example, using histogram-based segmentation, to create one or more zones representing a location and an area of the main ROI in the first image 100a in step 310. The main ROIs to be excluded from measurement can also be identified.

The main ROIs can be selected in step 315. A manual input from a user can be used to select the main ROIs or an automated process can be used to determine which of the localized main ROIs is of interest.

Once the main ROIs are segmented and selected, the normalized X-ray attenuation factor is determined for the main ROIs in step 320 as previously applied in the method 200.

As previously described, the ADRC process can determine a new set of parameters for the X-ray system when imaging the main ROI, which can include one or more of the tube voltage, tube current, focal spot size, pulse width, or other parameter that can be changed in real time between X-ray pulses. Notably, the library, further including information on various main ROIs, can be used by the ADRC process, wherein the main ROIs information includes materials and target CNR for optimal visibility. Thus, the main ROI information, current tube parameters (e.g., kV, mA, pulse width) and detected conditions (e.g., anode temperature of the X-ray tube), and the target CNR can be used to determine, via the ADRC process and the processing circuitry, the second X-ray exposure setting with optimized exposure parameters in step 325.

These new parameters can be implemented by the fluoroscopy system for use for the next X-ray pulse in step 330. The ADRC process can also calculate the second X-ray exposure setting that can only be set while the fluoroscopy system is not active, such as a beam filter selection. These parameters (non-real time parameters) can be set in the fluoroscopy system at an appropriate time. Subsequently, the second image 100b can be obtained in step 335.

FIG. 3B shows example images for a non-limiting example process flow overview for automatically adjusting the ADRC in the absence of an object, according to an embodiment of the present disclosure.

In an embodiment, the step 230 of the method 200 (and similarly in the step 320 of the method 300) can be performed such that the background ROI or the main ROI pixel intensity values are averaged with pixel intensity values of non-selected secondary regions in the first image 100a. That is, the non-selected secondary regions can be pixels outside of the background ROI or the main ROI. A predetermined first weight or importance value can be assigned to the non-selected secondary regions to increase or decrease their contribution to the determined normalized X-ray attenuation factor. Similarly, a predetermined corresponding second weight can be assigned to the background ROI or the main ROI. This can benefit the obtained second image 100b by adjusting for any over- or under-exposed regions in the first image 100a that will be magnified upon obtaining the second image 100b.

For example, with reference to the first image 100a and the second image 100b of FIG. 1 and the method 200, the top-right corner of the first image 100a in FIG. 1 is noticeably brighter or more exposed compared to the rest of the first image 100a. After performing the ADRC process using just the segmented guide wire 110 and the background ROI and obtaining the second image 100b in FIG. 1, the same top-right corner can be considered over-exposed, thus obscuring any potentially important information in that location. Therefore, to mitigate this over-exposure, pixel intensity values of the non-selected secondary regions (including those of the brighter non-selected secondary region's pixels in the top-right of the first image 100a in FIG. 1) can be averaged together with the background ROI pixel intensity values. Notably, a weight can be applied to the non-selected secondary region pixel intensity values to preserve the desired optimization of the CNR of the background ROI. For example, the weight can be 1 to 80%, or 5 to 75%, or 5%, or 10%, or 15%, or 20%, or 25%, or 30%, or 35%, or 40%, or 45%, or 50%, or 75%. By adjusting the weight, the degree of over-exposure of the top-right of the second image 100b in FIG. 1 can be adjusted to provide an improved contrast of the guide wire 110 without as much over-exposure elsewhere. It may be appreciated that a portion of the non-selected secondary regions can similarly be excluded from the ADRC process. The selected portions of the non-selected secondary regions can be selected manually, or via machine vision as previously described. In another example of machine vision, a measuring field around the guide wire 110 can be determined (in combination or separately from the background ROI) and pixel intensity values of the measuring field can be averaged with the pixel intensity values of the background ROI.

Figure 4:
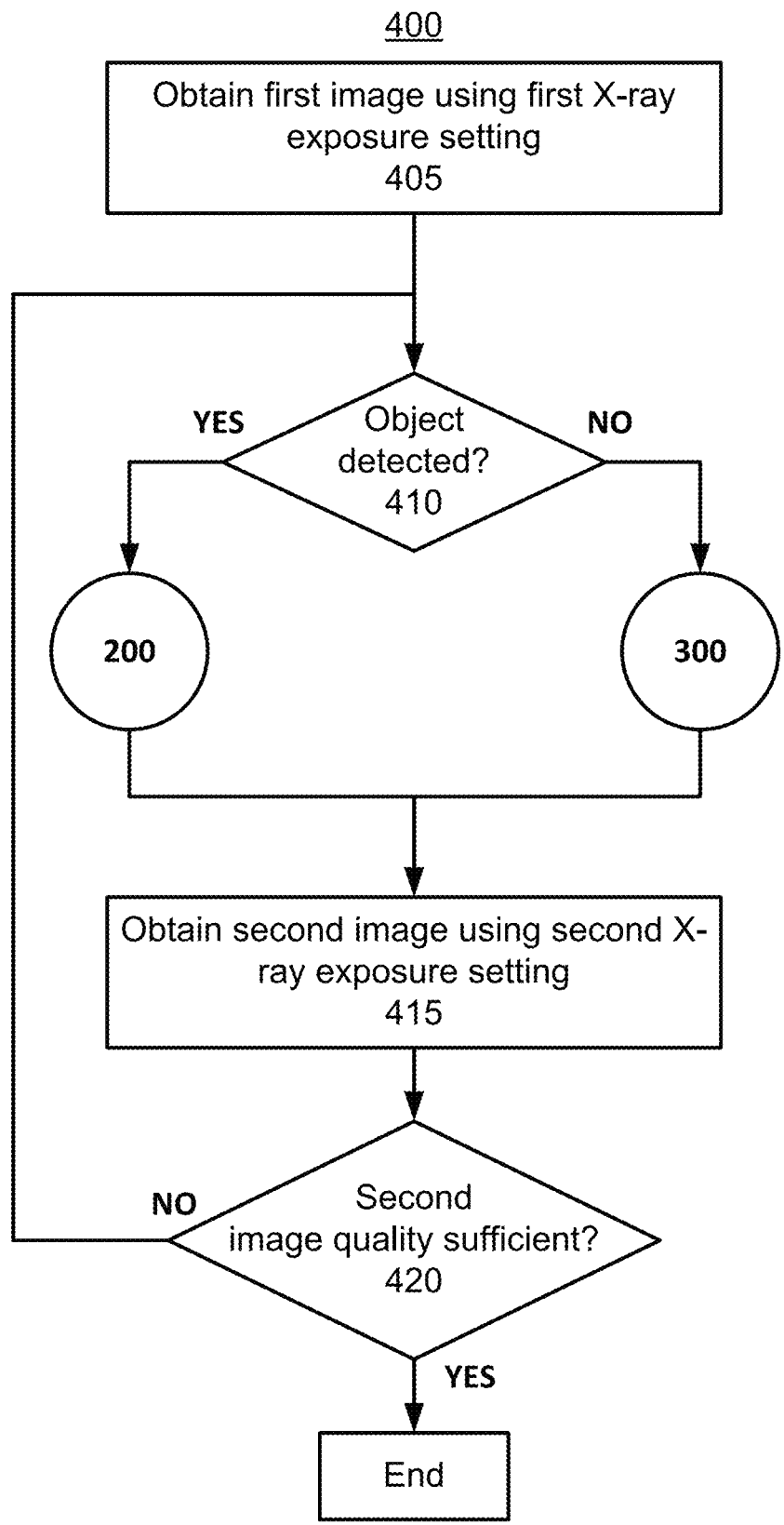
FIG. 4 shows a non-limiting example of a flow chart for a method of generating and applying optimized exposure parameters in a fluoroscopy system with iteration, according to an embodiment of the present disclosure.

FIG. 4 shows a non-limiting example of a flow chart for a method 400 of generating and applying optimized exposure parameters in the fluoroscopy system with iteration, according to an embodiment of the present disclosure. In an embodiment, a first image can be obtained in step 405 via the fluoroscopy system using the first X-ray exposure setting. In step 410, the method 200 can be performed when an object is detected in the first image to localize and segment the object of interest, as well as select the background ROI and determine the normalized X-ray attenuation factor of the background ROI in order to determine the second X-ray exposure setting. When an object is not detected, the method 300 can be performed to localize and segment a main ROI, as well as determine the normalized X-ray attenuation factor of the main ROI in order to determine the second X-ray exposure setting. In step 415, a second image can be obtained. In step 420, when the second image is determined to be of sufficient quality, such as when a predetermined CNR has been reached, the user can identify the object or region of interest in the second image and the method 400 can end. When the second image is determined to be of insufficient quality, such as when the user cannot distinguish objects or main ROIs in the second image, the method 400 can repeat at step 410 using the second image as the image for identifying if an object is present.

Advantageously, the described methods have sensitivity to actual objects or regions of interest within an image, the regions these objects occupy, and exclusion of other objects. Other methods can apply a fixed region of the image for ADRC and assume it contains the object of interest.

Figure 5:
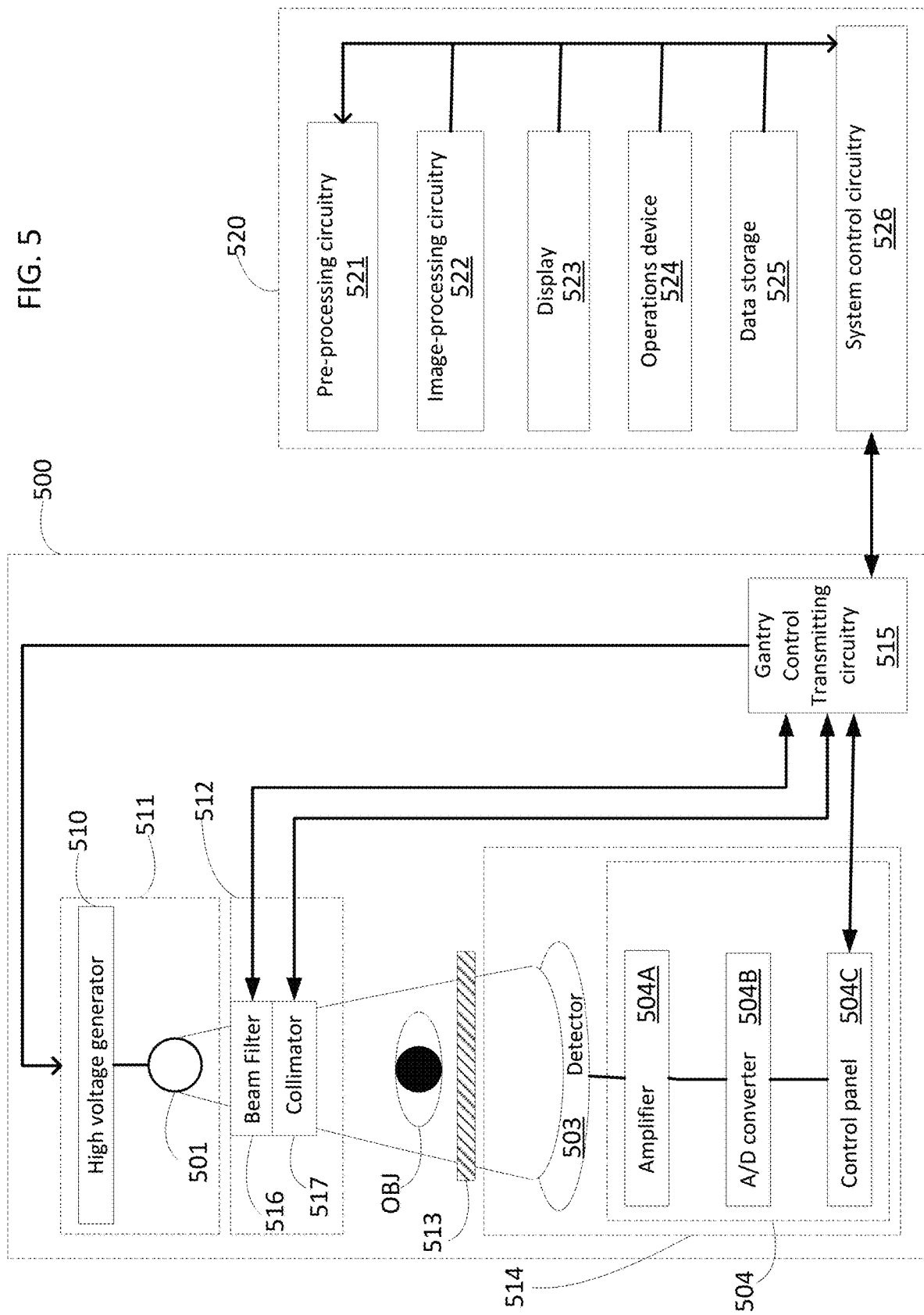
FIG. 5 is a block diagram of an exemplary X-ray apparatus, according to an embodiment of the present disclosure.

FIG. 5 is a block diagram of an exemplary X-ray apparatus that can be used to perform the methods described herein, e.g., methods 200, 300, and 400, according to an embodiment of the present disclosure. The X-ray apparatus includes a gantry 500 and a console 520. The gantry 500 includes an X-ray source system 511, a beam-shaping system 512, a patient table 513, a detection system 514, and a gantry control transmission circuitry 515.

The X-ray source system 511 includes a high voltage generator 510 and an X-ray tube 501. The high voltage generator 510 applies a high voltage to the X-ray tube 501 under the control of the gantry control transmission circuitry 515, and supplies a filament current to the X-ray tube 501 under the control of the gantry control transmission circuitry 515. The X-ray tube 501 generates X-rays to irradiate an object OBJ upon receiving a trigger from the high voltage generator 510.

The collimation system 512 includes a beam filter/attenuator 516 which modifies the spectrum of the X-ray beam from the X-ray tube 501. A collimator 517 opens and closes in accordance with a field of view selected at the time of the operation. The collimation system 512 forms an X-ray beam and irradiates the object OBJ with X-rays.

The detection system 514 includes a two-dimensional array of detection elements (pixels) configured to absorb the X-ray transmitted through the object OBJ and generate an electrical charge signal proportional to the absorbed X-ray intensity. The electrical signal of each pixel is amplified and converted to a digital number by A/D converters.

For example, the detection system 514 includes the detector 503 and a data acquisition system (DAS) 504. The detector 503 detects the X-rays generated from the X-ray tube 501. The detector 503 is equipped with a plurality of detection elements arrayed two-dimensionally. Each detection element detects the X-rays generated from the X-ray tube 501 and generates an electrical signal (current signal) corresponding to the intensity of the detected X-rays.

The generated electrical signal is supplied to the DAS 504. The DAS 504 includes an amplifier 504A, an A/D converter 504B, and a control panel 504C. The DAS 504 reads out electrical signals via the detector 503 and obtains the readout electrical signals, via the control panel 504C. The gantry control transmission circuitry 515 controls the high voltage generator 510, the attenuator 516, the collimator 517, and the control panel 504 to execute X-ray imaging.

The console 520 includes pre-processing circuitry 521, image-processing circuitry 522, a display 523, an operation device 524, data storage 525, and system control circuitry 526.

The pre-processing circuitry 521 executes pre-processing, such as sensitivity correction for raw data supplied from the detection system 514, via the gantry control transmission circuitry 515.

The image-processing circuitry 522 can perform the image-processing methods described herein, including methods 200, 300, and 400.

The display 523 displays the image generated by the image-processing circuitry 522.

The operation circuitry 524 accepts various types of commands and information inputs from a user, via an input device.

The data storage (memory) 525 stores the raw data and various types of data, such as projection data and images. In addition, the data storage 525 stores control programs for the X-ray apparatus, and control programs for performing the image-processing methods described herein.

The system control circuitry 526 functions as the main circuitry of the X-ray apparatus. The system control circuitry 526 reads out control programs stored in the data storage 525 and loads the programs into the memory. The system control circuitry 526 controls the respective circuitry in the X-ray apparatus in accordance with the loaded control programs.

In the preceding description, specific details have been set forth, such as a particular geometry of a processing system and descriptions of various components and processes used therein. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same functional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described embodiment. Various additional operations may be performed and/or described operations may be omitted in additional embodiments.

Embodiments of the present disclosure may also be as set forth in the following parentheticals.

(1) An imaging apparatus, comprising: processing circuitry configured to obtain a first image including projection data representing an intensity of X-rays, emitted from an X-ray source, detected by a plurality of detectors at a first X-ray exposure setting, based on a detection result of a first object in the first image: determine a background region of interest (ROI) around the first object, the background ROI including background ROI pixels having a first intensity value corresponding to the intensity of the X-rays, and convert, for each pixel of the background ROI pixels, the first intensity values of the background ROI pixels to a normalized X-ray attenuation factor, and determine a second X-ray exposure setting for use in obtaining a second image based on the background ROI pixels converted to the normalized X-ray attenuation factor.

(2) The apparatus of (1), wherein the processing circuitry is further configured based on the detection result of the first object in the first image: determine an area of a main ROI, the main ROI including main ROI pixels having a second intensity value corresponding to the intensity of the X-rays, and convert, for each pixel of the main ROI pixels, the second intensity values of the main ROI pixels to the normalized X-ray attenuation factor, and determine the second X-ray exposure setting for use in obtaining a second image based on the main ROI pixels converted to the normalized X-ray attenuation factor.

(3) The apparatus of (2), wherein the processing circuitry is further configured to determine a secondary ROI in the first image, the secondary ROI including secondary pixels having a third intensity value corresponding to the intensity of the X-rays, and wherein the processing circuitry is further configured to convert the first intensity values or the second intensity values to the normalized X-ray attenuation factor by applying a first weight to the third intensity values of the secondary pixels, determining, for each pixel of the background ROI pixels or the main ROI pixels, a mixed weight intensity value including the weighted third intensity value averaged with either the first intensity value or the second intensity value, and converting, for each pixel of the background ROI pixels or the main ROI pixels, the mixed weight intensity values of the background ROI pixels or the main ROI pixels to the normalized X-ray attenuation factor.

(4) The apparatus of either (2) or (3), wherein the processing circuitry is further configured to identify a second object in the first image, and exclude the second object when determining the second X-ray exposure setting.

(5) The apparatus of any one of (1) to (4), wherein the first object and the background ROI are identified using machine vision.

(6) The apparatus of (5), wherein the machine vision comprises a trained neural network.

(7) The apparatus of (2), wherein the first object, the background ROI, and the main ROI are identified using machine vision.

(8) The apparatus of (2), wherein the processing circuitry is further configured to determine the second X-ray exposure setting using an automatic dose rate control process.

(9) The apparatus of (2), wherein the processing circuitry is further configured to repeat: determining the background ROI around the first object, converting, for each pixel of the background ROI pixels, the first intensity values of the background ROI pixels to the normalized X-ray attenuation factor, and determining the second X-ray exposure setting for use in obtaining a second image based on the background ROI pixels converted to the normalized X-ray attenuation factor

(10) A method of adjusting dose rate in an imaging apparatus, comprising: obtaining a first image including projection data representing an intensity of X-rays detected by a plurality of detectors at a first X-ray exposure setting, the X-rays being emitted from an X-ray source; based on a detection result of a first object in the first image: determining a background region of interest (ROI) around the first object, the background ROI including background ROI pixels having a first intensity value corresponding to the intensity of the X-rays; and converting, for each pixel of the background ROI pixels, the first intensity values of the background ROI pixels to a normalized X-ray attenuation factor; and determining a second X-ray exposure setting for use in obtaining a second image based on the background ROI pixels converted to the normalized X-ray attenuation factor.

(11) The method of (10), further comprising: based on the detection result of the first object in the first image: determining an area of a main ROI, the main ROI including main ROI pixels having a second intensity value corresponding to the intensity of the X-rays; and converting, for each pixel of the main ROI pixels, the second intensity values of the main ROI pixels to the normalized X-ray attenuation factor; and determining the second X-ray exposure setting for use in obtaining a second image based on the main ROI pixels converted to the normalized X-ray attenuation factor.

(12) The method of (11), further comprising: determining a secondary ROI in the first image, the secondary ROI including secondary pixels having a third intensity value corresponding to the intensity of the X-rays, and converting the first intensity values or the second intensity values to the normalized X-ray attenuation factor further comprises applying a first weight to the third intensity values of the secondary pixels, determining, for each pixel of the background ROI pixels or the main ROI pixels, a mixed weight intensity value including the weighted third intensity value averaged with either the first intensity value or the second intensity value, and converting, for each pixel of the background ROI pixels or the main ROI pixels, the mixed weight intensity values of the background ROI pixels or the main ROI pixels to the normalized X-ray attenuation factor.

(13) The method of either (11) or (12), further comprising: identifying a second object in the first image, and excluding the second object when determining the second X-ray exposure setting.

(14) The method of any one of (10) to (13), wherein the first object and the background ROI are identified using machine vision.

(15) The method of (11), wherein the second X-ray exposure setting is determined using an automatic dose rate control process.

(16) The method of (11), further comprising: repeating: determining the background ROI around the first object; converting, for each pixel of the background ROI pixels, the first intensity values of the background ROI pixels to the normalized X-ray attenuation factor; and determining the second X-ray exposure setting for use in obtaining a second image based on the background ROI pixels converted to the normalized X-ray attenuation factor.

(17) A non-transitory computer-readable storage medium including executable instructions, which when executed by circuitry, cause the circuitry to perform a method of adjusting dose rate in an imaging apparatus, comprising: obtaining a first image including projection data representing an intensity of X-rays detected by a plurality of detectors at a first X-ray exposure setting, the X-rays being emitted from an X-ray source; based on a detection result of a first object in the first image: determining a background region of interest (ROI) around the first object, the background ROI including background ROI pixels having a first intensity value corresponding to the intensity of the X-rays; and converting, for each pixel of the background ROI pixels, the first intensity values of the background ROI pixels to a normalized X-ray attenuation factor; and determining a second X-ray exposure setting for use in obtaining a second image based on the background ROI pixels converted to the normalized X-ray attenuation factor.

(18) The computer-readable storage medium of (17), wherein the method further comprises: based on the detection result of the first object in the first image: determining a location and an area of a main ROI, the main ROI including main ROI pixels having a second intensity value corresponding to the intensity of the X-rays; and converting, for each pixel of the main ROI pixels, the second intensity values of the main ROI pixels to the normalized X-ray attenuation factor; and determining the second X-ray exposure setting for use in obtaining a second image based on the main ROI pixels converted to the normalized X-ray attenuation factor.

(19) The computer-readable storage medium of (18), wherein the method further comprises determining a secondary ROI in the first image, the secondary ROI including secondary pixels having a third intensity value corresponding to the intensity of the X-rays, and converting the first intensity values or the second intensity values to the normalized X-ray attenuation factor further comprises applying a first weight to the third intensity values of the secondary pixels, determining, for each pixel of the background ROI pixels or the main ROI pixels, a mixed weight intensity value including the weighted third intensity value averaged with either the first intensity value or the second intensity value, and converting, for each pixel of the background ROI pixels or the main ROI pixels, the mixed weight intensity values of the background ROI pixels or the main ROI pixels to the normalized X-ray attenuation factor.

(20) The computer-readable storage medium of (18), wherein the method further comprises: identifying a second object in the first image, and excluding the second object when determining the second X-ray exposure setting.

(21) The apparatus of (1), wherein the processing circuitry is further configured to based on the detection result of the first object in the first image: determine a location of the first object in the first image; and segment the first object in the first image.

(22) The apparatus of (1), wherein the processing circuitry is further configured to obtain a second image using the second X-ray exposure setting.

(23) The apparatus of (1), wherein the normalized X-ray attenuation factor corresponds to an equivalent thickness.

(24) The apparatus of (23), wherein the equivalent thickness corresponds to a water equivalent thickness.

(25) The apparatus of (23), wherein the equivalent thickness corresponds to an equivalent thickness including at least two materials.

(26) The apparatus of (1), wherein the converting the first intensity values of the background ROI pixels to a normalized X-ray attenuation factor further comprises: generating a material decomposition map of the background ROI; and normalizing each pixel of the background ROI pixels using a material decomposition value at the corresponding location in the material decomposition map.

(27) The method of (10), further comprising: based on the detection result of the first object in the first image: determining a location of the first object in the first image; and segmenting the first object in the first image.

(28) The method of (10), further comprising: obtaining a second image using the second X-ray exposure setting.

(29) The method of (10), wherein the normalized X-ray attenuation corresponds to an equivalent thickness.

(30) The method of (29), wherein the equivalent thickness corresponds to a water equivalent thickness.

(31) The method of (29), wherein the equivalent thickness corresponds to an equivalent thickness including at least two materials.

(32) The method of (10), wherein the converting the first intensity values of the background ROI pixels to a normalized X-ray attenuation factor further comprises: generating a material decomposition map of the background ROI; and normalizing each pixel of the background ROI pixels using a material decomposition value at the corresponding location in the material decomposition map.

(33) The computer-readable storage medium of (18), wherein the method further comprises: based on the detection result of the first object in the first image: determining a location of the first object in the first image; and segmenting the first object in the first image.

(34) The computer-readable storage medium of (18), further comprising: obtaining a second image using the second X-ray exposure setting.

(35) The computer-readable storage medium of (18), wherein the normalized X-ray attenuation factor corresponds to an equivalent thickness.

(36) The computer-readable storage medium of (35), wherein the equivalent thickness corresponds to a water equivalent thickness.

(37) The computer-readable storage medium of (35), wherein the equivalent thickness corresponds to an equivalent thickness including at least two materials.

(38) The computer-readable storage medium of (18), wherein the converting the first intensity values of the background ROI pixels to a normalized X-ray attenuation factor further comprises: generating a material decomposition map of the background ROI; and normalizing each pixel of the background ROI pixels using a material decomposition value at the corresponding location in the material decomposition map.

(39) The apparatus of either (1) or (2), wherein the area of the main ROI is determined using histogram-based segmentation.

(40) The apparatus of (2), wherein the converting includes averaging the weighted third intensity values with weighted first intensity values or weighted second intensity values.

(41) The method of either (10) or (11), wherein the area of the main ROI is determined using histogram-based segmentation.

(42) The method of (12), wherein the converting includes averaging the weighted third intensity values with weighted first intensity values or weighted second intensity values.

(43) The computer-readable storage medium of (17) or (18), wherein the area of the main ROI is determined using histogram-based segmentation.

(44) The computer-readable storage medium of (18), wherein the converting includes averaging the weighted third intensity values with weighted first intensity values or weighted second intensity values.

(45) The apparatus of (3), wherein the secondary ROI is determined using a Measuring Field.

(46) The method of (12), wherein the secondary ROI is determined using a Measuring Field.

(45) The computer-readable storage medium of (19), wherein the secondary ROI is determined using a Measuring Field.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the following claims.

What is claimed is:

1. An imaging apparatus, comprising:
   processing circuitry configured to
      obtain a first image including projection data representing an intensity of X-rays, emitted from an X-ray source, detected by a plurality of detectors at a first X-ray exposure setting,
      based on a detection result of a first object in the first image:
         determine a background region of interest (ROI) in a background around the first object, the background ROI being formed by pixels having a first intensity value corresponding to the intensity of the X-rays, and
         convert, for each pixel of the background ROI pixels, the first intensity values of the background ROI pixels to a normalized X-ray attenuation factor, and
      determine a second X-ray exposure setting for use in obtaining a second image based on the background ROI pixels converted to the normalized X-ray attenuation factor.

2. The apparatus of claim 1, wherein the processing circuitry is further configured to
   based on the detection result of the first object in the first image:
      determine an area of a main ROI, the main ROI including main ROI pixels having a second intensity value corresponding to the intensity of the X-rays, and convert, for each pixel of the main ROI pixels, the second intensity values of the main ROI pixels to the normalized X-ray attenuation factor, and determine the second X-ray exposure setting for use in obtaining a second image based on the main ROI pixels converted to the normalized X-ray attenuation factor.

3. The apparatus of claim 2, wherein the processing circuitry is further configured to determine a secondary ROI in the first image, the secondary ROI including secondary pixels having a third intensity value corresponding to the intensity of the X-rays, and wherein the processing circuitry is further configured to convert the first intensity values or the second intensity values to the normalized X-ray attenuation factor by applying a first weight to the third intensity values of the secondary pixels, determining, for each pixel of the background ROI pixels or the main ROI pixels, a mixed weight intensity value including the weighted third intensity value averaged with either the first intensity value or the second intensity value, and converting, for each pixel of the background ROI pixels or the main ROI pixels, the mixed weight intensity values of the background ROI pixels or the main ROI pixels to the normalized X-ray attenuation factor.

4. The apparatus of claim 2, wherein the processing circuitry is further configured to identify a second object in the first image, and exclude the second object when determining the second X-ray exposure setting.

5. The apparatus of claim 2, wherein the first object, the background ROI, and the main ROI are identified using machine vision.

6. The apparatus of claim 2, wherein the processing circuitry is further configured to determine the second X-ray exposure setting using an automatic dose rate control process.

7. The apparatus of claim 2, wherein the processing circuitry is further configured to repeat:

determining the background ROI around the first object, converting, for each pixel of the background ROI pixels, the first intensity values of the background ROI pixels to the normalized X-ray attenuation factor, and determining the second X-ray exposure setting for use in obtaining a second image based on the background ROI pixels converted to the normalized X-ray attenuation factor.

8. The apparatus of claim 1, wherein the first object and the background ROI are identified using machine vision.

9. The apparatus of claim 8, wherein the machine vision comprises a trained neural network.

10. A method of adjusting dose rate in an imaging apparatus, comprising:

obtaining a first image including projection data representing an intensity of X-rays detected by a plurality of detectors at a first X-ray exposure setting, the X-rays being emitted from an X-ray source;

based on a detection result of a first object in the first image:

determining a background region of interest (ROI) in a background around the first object, the background ROI being formed by pixels having a first intensity value corresponding to the intensity of the X-rays; and converting, for each pixel of the background ROI pixels, the first intensity values of the background ROI pixels to a normalized X-ray attenuation factor; and determining a second X-ray exposure setting for use in obtaining a second image based on the background ROI pixels converted to the normalized X-ray attenuation factor.

11. The method of claim 10, further comprising:

based on the detection result of the first object in the first image:

determining an area of a main ROI, the main ROI including main ROI pixels having a second intensity value corresponding to the intensity of the X-rays; and converting, for each pixel of the main ROI pixels, the second intensity values of the main ROI pixels to the normalized X-ray attenuation factor; and determining the second X-ray exposure setting for use in obtaining a second image based on the main ROI pixels converted to the normalized X-ray attenuation factor.

12. The method of claim 11, further comprising:

determining a secondary ROI in the first image, the secondary ROI including secondary pixels having a third intensity value corresponding to the intensity of the X-rays, and converting the first intensity values or the second intensity values to the normalized X-ray attenuation factor further comprises applying a first weight to the third intensity values of the secondary pixels, determining, for each pixel of the background ROI pixels or the main ROI pixels, a mixed weight intensity value including the weighted third intensity value averaged with either the first intensity value or the second intensity value, and converting, for each pixel of the background ROI pixels or the main ROI pixels, the mixed weight intensity values of the background ROI pixels or the main ROI pixels to the normalized X-ray attenuation factor.

13. The method of claim 11, further comprising:

identifying a second object in the first image, and excluding the second object when determining the second X-ray exposure setting.

14. The method of claim 11, further comprising:

repeating:

determining the background ROI around the first object;

converting, for each pixel of the background ROI pixels, the first intensity values of the background ROI pixels to the normalized X-ray attenuation factor; and determining the second X-ray exposure setting for use in obtaining a second image based on the background ROI pixels converted to the normalized X-ray attenuation factor.

15. The method of claim 10, wherein the first object and the background ROI are identified using machine vision.

16. The method of claim 11, wherein the second X-ray exposure setting is determined using an automatic dose rate control process.

17. A non-transitory computer-readable storage medium including executable instructions, which when executed by circuitry, cause the circuitry to perform a method of adjusting dose rate in an imaging apparatus, comprising:

obtaining a first image including projection data representing an intensity of X-rays detected by a plurality of detectors at a first X-ray exposure setting, the X-rays being emitted from an X-ray source;

based on a detection result of a first object in the first image:

determining a background region of interest (ROI) in a background around the first object, the background ROI being formed by pixels having a first intensity value corresponding to the intensity of the X-rays; and converting, for each pixel of the background ROI pixels, the first intensity values of the background ROI pixels to a normalized X-ray attenuation factor; and determining a second X-ray exposure setting for use in obtaining a second image based on the background ROI pixels converted to the normalized X-ray attenuation factor.

18. The non-transitory computer-readable storage medium according to claim 17, wherein the method further comprises:

based on the detection result of the first object in the first image:

determining a location and an area of a main ROI, the main ROI including main ROI pixels having a second intensity value corresponding to the intensity of the X-rays; and converting, for each pixel of the main ROI pixels, the second intensity values of the main ROI pixels to the normalized X-ray attenuation factor; and determining the second X-ray exposure setting for use in obtaining a second image based on the main ROI pixels converted to the normalized X-ray attenuation factor.

19. The non-transitory computer-readable storage medium according to claim 18, wherein the method further comprises:

determining a secondary ROI in the first image, the secondary ROI including secondary pixels having a third intensity value corresponding to the intensity of the X-rays, and converting the first intensity values or the second intensity values to the normalized X-ray attenuation factor further comprises applying a first weight to the third intensity values of the secondary pixels, determining, for each pixel of the background ROI pixels or the main ROI pixels, a mixed weight intensity value including the weighted third intensity value averaged with either the first intensity value or the second intensity value, and converting, for each pixel of the background ROI pixels or the main ROI pixels, the mixed weight intensity values of the background ROI pixels or the main ROI pixels to the normalized X-ray attenuation factor.

20. The non-transitory computer-readable storage medium according to claim 18, wherein the method further comprises:

identifying a second object in the first image, and excluding the second object when determining the second X-ray exposure setting.

21. An imaging apparatus, comprising:

processing circuitry configured to obtain a first image including projection data representing an intensity of X-rays, emitted from an X-ray source, detected by a plurality of detectors at a first X-ray exposure setting, based on a detection result of a first object in the first image:

determine a background region of interest (ROI) around the first object, the background ROI pixels having a first intensity value corresponding to the intensity of the X-rays, and convert, for each pixel of the background ROI pixels, the first intensity values of the background ROI pixels to a normalized X-ray attenuation factor, and determine a second X-ray exposure setting for use in obtaining a second image based on the background ROI pixels converted to the normalized X-ray attenuation factor, wherein the processing circuitry is further configured to based on the detection result of the first object in the first image:

determine an area of a main ROI, the main ROI including main ROI pixels having a second intensity value corresponding to the intensity of the X-rays, and convert, for each pixel of the main ROI pixels, the second intensity values of the main ROI pixels to the normalized X-ray attenuation factor, and determine the second X-ray exposure setting for use in obtaining a second image based on the main ROI pixels converted to the normalized X-ray attenuation factor.

22. A method of adjusting dose rate in an imaging apparatus, comprising:

obtaining a first image including projection data representing an intensity of X-rays detected by a plurality of detectors at a first X-ray exposure setting, the X-rays being emitted from an X-ray source;

based on a detection result of a first object in the first image:

determining a background region of interest (ROI) around the first object, the background ROI pixels having a first intensity value corresponding to the intensity of the X-rays; and converting, for each pixel of the background ROI pixels, the first intensity values of the background ROI pixels to a normalized X-ray attenuation factor; and determining a second X-ray exposure setting for use in obtaining a second image based on the background ROI pixels converted to the normalized X-ray attenuation factor, wherein the method further comprises:

based on the detection result of the first object in the first image:

determining an area of a main ROI, the main ROI including main ROI pixels having a second intensity value corresponding to the intensity of the X-rays; and converting, for each pixel of the main ROI pixels, the second intensity values of the main ROI pixels to the normalized X-ray attenuation factor; and determining the second X-ray exposure setting for use in obtaining a second image based on the main ROI pixels converted to the normalized X-ray attenuation factor.

23. A non-transitory computer-readable storage medium including executable instructions, which when executed by circuitry, cause the circuitry to perform a method of adjusting dose rate in an imaging apparatus, comprising:

obtaining a first image including projection data representing an intensity of X-rays detected by a plurality of detectors at a first X-ray exposure setting, the X-rays being emitted from an X-ray source;

based on a detection result of a first object in the first image:

determining a background region of interest (ROI) around the first object, the background ROI pixels having a first intensity value corresponding to the intensity of the X-rays; and converting, for each pixel of the background ROI pixels, the first intensity values of the background ROI pixels to a normalized X-ray attenuation factor; and determining a second X-ray exposure setting for use in obtaining a second image based on the background ROI pixels converted to the normalized X-ray attenuation factor, wherein the method further comprises:

based on the detection result of the first object in the first image:

determining an area of a main ROI, the main ROI including main ROI pixels having a second intensity value corresponding to the intensity of the X-rays; and converting, for each pixel of the main ROI pixels, the second intensity values of the main ROI pixels to the normalized X-ray attenuation factor; and determining the second X-ray exposure setting for use in obtaining a second image based on the main ROI pixels converted to the normalized X-ray attenuation factor.

* * * * *